(12) United States Patent
Kitamura et al.

(10) Patent No.: US 10,078,058 B2
(45) Date of Patent: Sep. 18, 2018

(54) X-RAY TALBOT CAPTURING APPARATUS

(71) Applicant: Konica Minolta, Inc., Chiyoda-ku, Tokyo (JP)

(72) Inventors: Mitsuharu Kitamura, Tokyo (JP); Yasunori Tsuboi, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 301 days.

(21) Appl. No.: 15/157,714

(22) Filed: May 18, 2016

(65) Prior Publication Data

US 2016/0349197 A1 Dec. 1, 2016

(30) Foreign Application Priority Data

May 28, 2015 (JP) .................. 2015-108208

(51) Int. Cl.
*G01N 23/04* (2018.01)
*G01N 23/20* (2018.01)
*G01N 23/20008* (2018.01)
*G21K 1/06* (2006.01)

(52) U.S. Cl.
CPC . *G01N 23/20075* (2013.01); *G01N 23/20008* (2013.01); *G21K 1/06* (2013.01); *G21K 2207/005* (2013.01)

(58) Field of Classification Search
CPC ........ G01N 23/00; G01N 23/04; G01N 23/20; G01N 23/20075; G01N 23/20008; G03H 5/00; G21K 2207/00; G21K 2207/05; A61B 6/484
USPC ...................................................... 378/36, 62
See application file for complete search history.

(56) References Cited

FOREIGN PATENT DOCUMENTS

| JP | 2007206075 A | 8/2007 |
|---|---|---|
| JP | 2012013530 A | 1/2012 |

*Primary Examiner* — Jurie Yun
(74) *Attorney, Agent, or Firm* — Cantor Colburn LLP

(57) ABSTRACT

An X-ray Talbot capturing apparatus is shown. A radiation source irradiates radiation through a plurality of gratings. A radiation detector captures a moire image. A holder which holds the gratings includes a receiving unit including a receiving surface with a curve and a pressing unit including a pressing surface with a curve. Each grating is held between the receiving surface and the pressing surface and bent in an arc shape with a point of the radiation source as a center. An elastic member is positioned between a first surface of the grating and the pressing surface or a second surface of the grating opposite of the first surface and the receiving surface. An opening is provided in the holder and the elastic member so as not to block radiation irradiated on the grating.

10 Claims, 9 Drawing Sheets

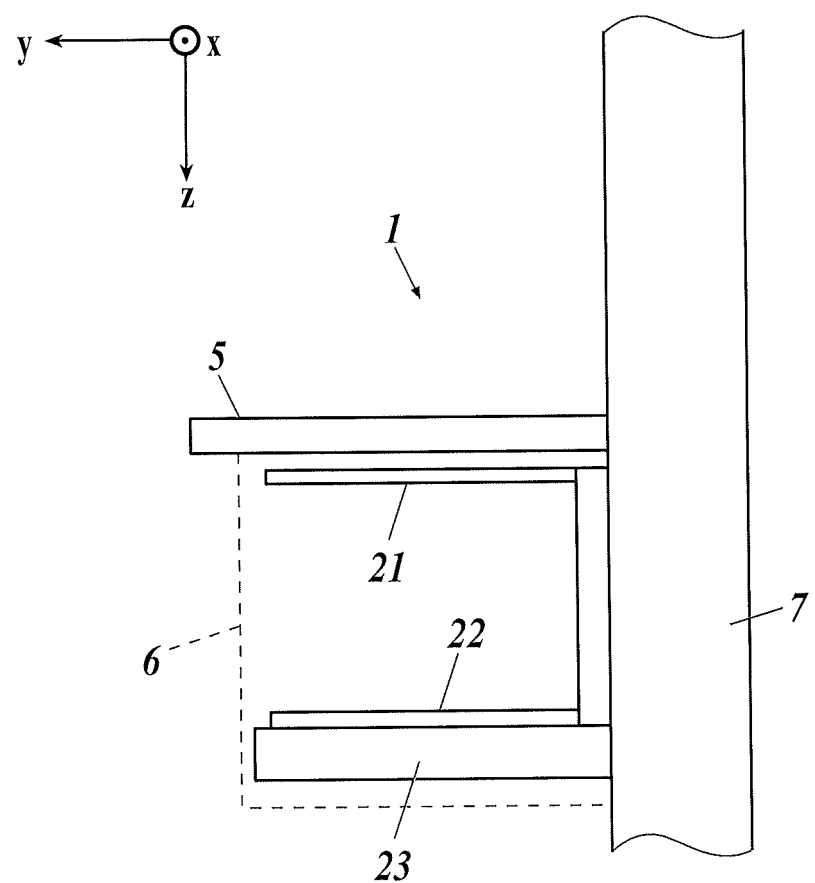

X-RAY TALBOT CAPTURING APPARATUS

CROSS REFERENCE TO RELATED APPLICATIONS

The present U.S. patent application claims priority under the Paris Convention of Japanese Patent Application No. 2015-108208 filed on May 28, 2015 the entirety of which is incorporated herein by reference.

BACKGROUND OF THE INVENTION

Field of the Invention

The present invention relates to an X-ray Talbot capturing apparatus using a Talbot interferometer or Talbot-Lau interferometer.

Description of Related Art

There is an X-ray capturing apparatus which uses a Talbot interferometer or Talbot-Lau interferometer and a radiation detector (Flat Panel Detector: FPD) to capture and image a phase shift of an X-ray generated when the X-ray passes through an object (For example, Japanese Patent Application Laid-Open Publication No. 2007-206075, Japanese Patent Application Laid-Open Publication No. 2012-13530). Such X-ray image capturing apparatuses which use the Talbot interferometer or Talbot-Lau interferometer is called a X-ray Talbot capturing apparatus.

The X-ray Talbot capturing apparatus includes a first grating (also called G1 grating, etc.) and a second grating (G2 grating, etc.) provided with slits at a certain interval (when the Talbot-Lau interferometer is used, a ray source grating (G0 grating, multi gratin) is also included). The second grating is positioned in the position where a self-image of the first grating is focused at a certain interval downstream of the X-ray irradiating direction of the first grating by emitting the X-ray to the first grating from the X-ray source. The second grating is positioned so that the extending direction of the slit in the second grating is slightly tilted with respect to the extending direction of the slit in the first grating. With this, a moire fringe is formed on the second grating. The image with the moire fringe superimposed (hereinafter referred to as moire image) is detected with the X-ray detector positioned downstream of the second grating and captured.

When the subject is positioned between the X-ray source (or ray source grating) and the first grating or the first grating and the second grating, the moire fringe is distorted by the subject. Therefore, a plurality of moire images are captured with the X-ray Talbot capturing apparatus while relatively moving the first grating and the second grating (fringe scanning method) and then image processing is performed to analyze the moire images to reconstruct and generate images such as a differential phase image, absorption image, small angle scattering image, etc. Alternatively, one moire image including the subject can be captured with the X-ray Talbot image capturing apparatus, and the image processing can be performed to perform Fourier transform on the moire image to reconstruct and generate the differential phase image (Fourier transforming method).

In the X-ray Talbot capturing apparatus, the radiation irradiated from the radiation source (or the radiation which is irradiated from the radiation source and passes the ray source grating) normally spreads in a cone beam shape, and when the grating is formed in a flat plane shape, the problem of vignetting occurs in the periphery of the grating. In other words, although illustration is omitted, when the slit S of the grating (see later described FIG. 3) is formed to pass radiation entering the radiation entering surface of the grating in the normal vector direction, the radiation enters the radiation entering surface in a direction tilted with respect to the normal vector direction in the periphery of the grating. Therefore, the rate of passing of the radiation becomes worse in the periphery of the grating than the center of the grating.

Therefore, for example, Japanese Patent Application Laid-Open Publication No. 2007-206075, Japanese Patent Application Laid-Open Publication No. 2012-13530 describe a configuration in which the first grating and the second grating (or ray source grating) are curved. In other words, according to the method shown in FIG. 6 of Japanese Patent Application Laid-Open Publication No. 2007-206075 both edges of the grating are pressed in a direction toward the radiation source, the inner side is pressed in the opposite direction, and the grating is curved. According to the method shown in FIG. 7 of Japanese Patent Application Laid-Open Publication No. 2007-06075, with both edges of the grating fixed, the pressure applied to the radiation entering surface of the grating is set differently from the pressure applied to the radiation exiting surface (surface opposite of the radiation entering surface) to bend the grating.

According to Japanese Patent Application Laid-Open Publication No. 2012-13530, a plurality of plate shaped small gratings are aligned and placed between a first and second supporting substrate to form a combined grating plate. The combined grating plate is placed between a concave surface stage and a convex surface stage to bend the combined grating plate. According to the above configuration, the radiation enters the radiation entering surface in the normal vector direction in any portion of the radiation entering surface of the grating in the bent combined grating plate. Therefore, this prevents vignetting.

However, when the grating is formed with a hard material such as a silicon wafer, if the method shown in FIG. 6 of Japanese Patent Application Laid-Open Publication No. 2007-206075 is employed, strong force needs to be applied to the grating to bend the hard grating. However, if both edges of the grating and points on the inside are pressed with such strong force (in other words, contact by point), the grating may break and be damaged. If the method shown in FIG. 7 of Japanese Patent Application Laid-Open Publication No. 2007-206075 is employed, it is necessary to form a space with high airtightness and then vacuum the space in at least one side of the grating, which is not practical.

According to the method described in Japanese Patent Application Laid-Open Publication No. 2012-13530, a plurality of small gratings are placed between the first and second supporting substrates to form one combined grating plate, and the radiation is absorbed by the first and second supporting substrates. Therefore, the signal value of the differential phase image, etc. reconstructed and generated from the moire image captured as described above reduces and the S/N ratio of the differential phase image becomes worse.

Therefore, in the X-ray Talbot capturing apparatus, it is preferable to form the first grating and the second grating (or the ray source grating) by bending one flat plate grating formed with silicon wafer or the like. Moreover, it is desired that the damage due to breaking does not occur, the radiation is not blocked by the members other than the grating and the grating is accurately bent at a certain curvature.

BRIEF SUMMARY OF THE INVENTION

The present invention has been made in consideration of the above problems, and one of the main objects is to provide an X-ray Talbot capturing apparatus in which the plurality of gratings such as a first grating and a second grating are not damaged and a plurality of gratings can be accurately curved to suitably pass radiation without causing vignetting.

In order to achieve at least one of the above-described objects, according to an aspect of the present invention, there is provided an X-ray Talbot capturing apparatus including: a plurality of gratings in which slits are formed; a radiation source which irradiates radiation to pass through the plurality of gratings; a radiation detector which captures a moire image; and a holder which holds the gratings, wherein, the holder includes a receiving unit including a receiving surface with a curve and a pressing unit including a pressing surface with a curve; each grating is held between the receiving surface of the receiving unit and the pressing surface of the pressing unit of the holder and bent in an arc shape with a point of the radiation source as a center; an elastic member is positioned between a first surface of the grating and the pressing surface of the pressing unit or a second surface of the grating opposite of the first surface and the receiving surface of the receiving unit; and an opening is provided in each of the receiving unit and the pressing unit of the holder and the elastic member so as not to block radiation irradiated on the grating.

According to the Talbot capturing apparatus of the present invention, the plurality of gratings such as a first grating and a second grating are not damaged and a plurality of gratings can be accurately curved to suitably pass radiation without causing vignetting. Therefore, it is possible to accurately capture a moire image with the X-ray Talbot capturing apparatus and to accurately reconstruct the moire image to accurately generate a differential phase image.

BRIEF DESCRIPTION OF THE DRAWINGS

The present invention will become more fully understood from the detailed description given hereinbelow and the appended drawings, and thus are not intended to define the limits of the present invention, and wherein;

FIG. 4 is a diagram describing a configuration in a second cover unit in a lower portion of the X-ray Talbot capturing apparatus of the present embodiment;

DETAILED DESCRIPTION OF PREFERRED EMBODIMENTS

An embodiment of a Talbot capturing apparatus of the present invention is described with reference to the drawings.

Figure 1:
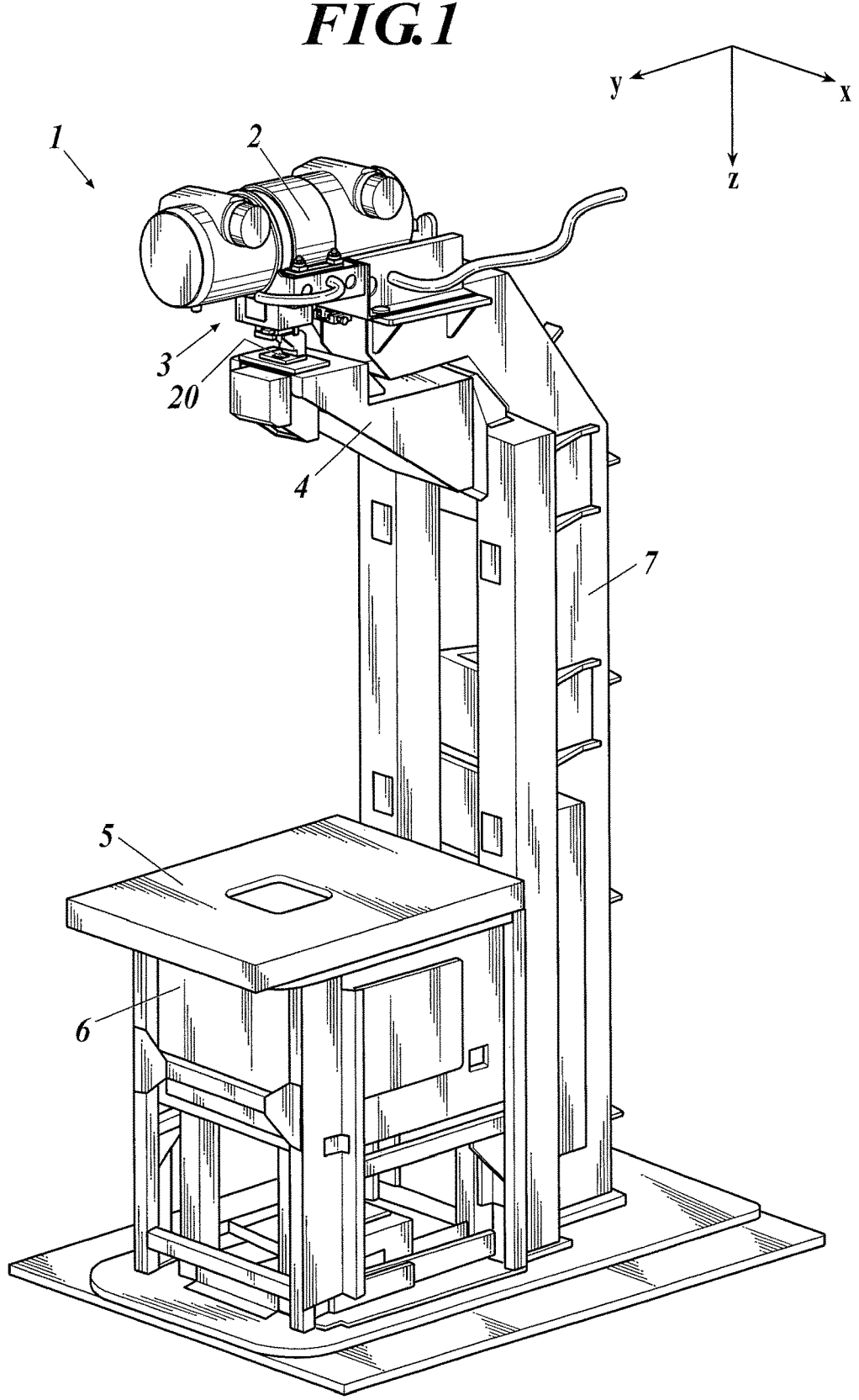
FIG. 1 is a perspective view showing an entire X-ray Talbot capturing apparatus of the present embodiment.

FIG. 1 is a perspective view showing an entire X-ray Talbot capturing apparatus of the present embodiment. As shown in FIG. 1, the X-ray Talbot capturing apparatus 1 of the present embodiment includes, a radiation source 2, a first cover unit 3 including a later described ray source grating 20, a supporting portion 4 which supports a first cover unit 3, etc., a subject stage 5, a second cover unit 6 including a later-described first grating 21, a second grating 22, and a radiation detector 23 (see later-described FIG. 4), and a column 7.

Figure 2:
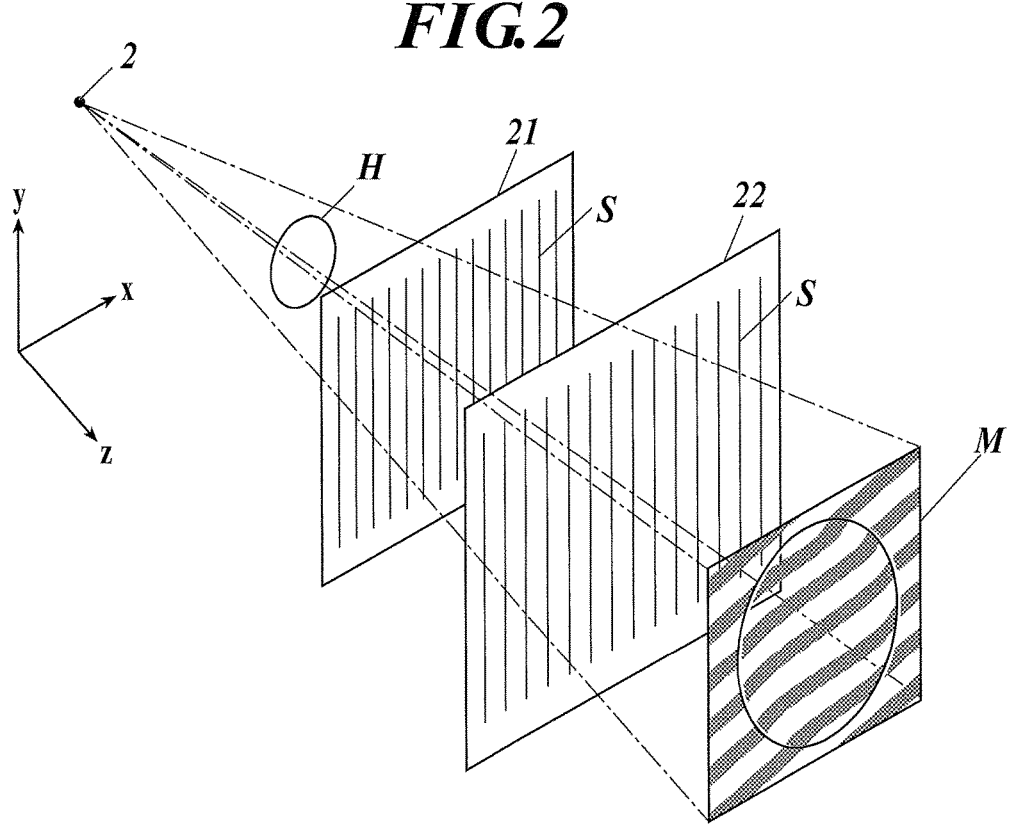
FIG. 2 is a diagram describing the principle of a Talbot interferometer and a Talbot-Lau interferometer.

Here, the principle common to the Talbot interferometer and the Talbot-Lau interferometer used in the X-ray Talbot capturing apparatus 1 is described using FIG. 2. FIG. 2 describes an example using the Talbot interferometer, and basically, the same description applies for the Talbot-Lau interferometer.

In the Talbot interferometer, the radiation source 2, the first grating 21, and the second grating 22 are positioned in order in the radiation irradiating direction (in other words, z-direction). Although illustration is omitted, a ray source grating 20 (see FIG. 1) is positioned near the radiation source 2 in the Talbot-Lau interferometer. As shown in FIG. 2, in the Talbot interferometer and the Talbot-Lau interferometer, a subject H is positioned in a position upstream of the first grating 21 in the radiation irradiating direction (in other words, z-direction). Although illustration is omitted, the subject H can be positioned in the position downstream of the first grating 21 in the radiation irradiating direction.

Figure 3:
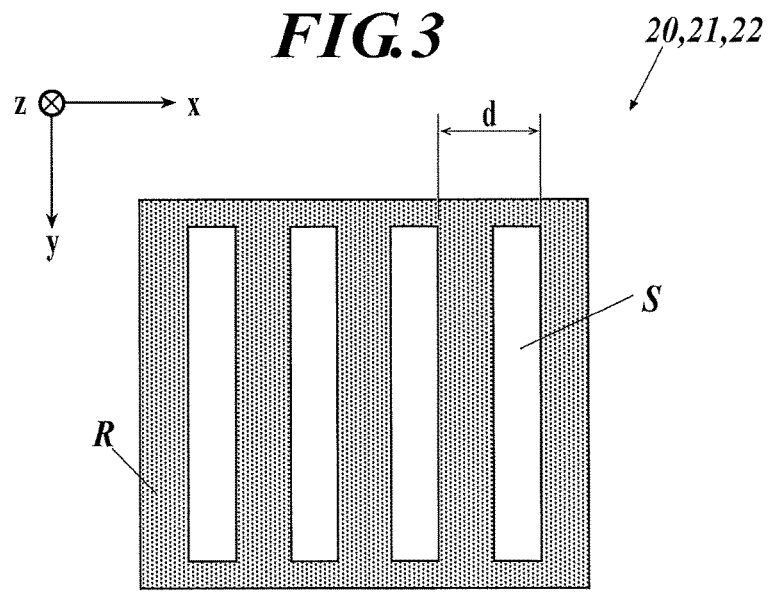
FIG. 3 is a diagram describing a plurality of slits provided to be arranged in a predetermined interval in a first grating, a second grating, and a ray source grating.

As shown in FIG. 3, in the first grating 21 and the second grating 22 (in a Talbot-Lau interferometer, the ray source grating 20 also) a plurality of slits S are formed aligned in a predetermined interval d in a x-direction orthogonal to the z-direction which is the radiation irradiating direction. The predetermined interval d is different in each of the first grating 21, the second grating 22, and the ray source grating 20. FIG. 3 describes the slit S relatively and greatly larger than the grating to make the slit S easily viewable.

Then, the radiation (in the Talbot-Lau interferometer, the radiation irradiated from the radiation source 2 and multiplied by the ray source grating 20) irradiated from the radiation source 2 passes the first grating 21, and the passed radiation focuses an image at a certain interval in the z-direction. This image is called a self-image (also called a grating image). The self-image is formed in a certain interval in the z-direction, and this is called the Talbot effect.

As shown in FIG. 2, the second grating 22 is positioned in the position where the self-image of the first grating 21 is focused. Here, the second grating 22 is positioned so that the extending direction of the slit S of the second grating 22 (in other words, y-axis direction in FIG. 2) forms a slight angle with respect to the extending direction of the slit S of the first grating 21. With such positioning, a moire image Mo consisting of only the moire fringe appears on the second grating 22. If the moire image Mo is drawn on the second grating 22, the moire fringe and the slit S are mixed, and the diagram becomes difficult to understand. Therefore, in FIG. 2, the moire image Mo is drawn separated from the second grating 22, but actually the moire image Mo is formed on or downstream the second grating 22.

When there is a subject H within the range of the irradiation of radiation, the phase of the radiation is shifted by the subject H. Therefore, there is disorder in the moire fringe of the moire image Mo with the edge of the subject as the border, and the moire image Mo with the disorder by the subject H as shown in FIG. 2 appears on or downstream of the second grating 22.

With this, the principle of the Talbot interferometer and the Talbot-Lau interferometer is described. The radiation detector 23 (see later described FIG. 4) positioned downstream of the second grating 22 captures the above-described moire image Mo. According to the present embodiment, the X-ray Talbot capturing apparatus 1 is configured based on this principle.

The configuration of the X-ray Talbot capturing apparatus 1 of the present embodiment is described below. According to the present embodiment, the X-ray Talbot capturing apparatus 1 uses a Talbot-Lau interferometer including the ray source grating 20. The description below similarly applies to the X-ray Talbot capturing apparatus using the Talbot interferometer including only the first grating 21 and the second grating 22 without the ray source grating 20.

The description below describes a configuration in which the X-ray Talbot capturing apparatus 1 is configured so that the radiation source 2 provided in the upper side irradiates radiation to the subject below as shown in FIG. 1. The present invention is not limited to the above, and the radiation can be emitted from the radiation source 2 in a horizontal direction or arbitrary direction to capture the moire image Mo of the subject.

The radiation source 2 of the present embodiment includes a radiation source such as a Coolidge X-ray source or a rotating anode X-ray source which is widely used in medical practice. Alternatively, other types of radiation sources (tube) can be used.

According to the present embodiment, a ray source grating 20 is provided downstream of the radiation source 2 in the radiation irradiating direction (in other words, z-direction). In order to prevent the vibration of the radiation source 2 from transmitting to the ray source grating 20, the ray source grating 20 is not attached to the radiation source 2, and is attached to a fixing member 4 attached to a support 7. Although illustration is omitted, in addition to the ray source grating 20, a filter (additional filter) to change the state of the radiation passing through the ray source grating or the irradiation field focus to focus the irradiation field of the irradiated radiation is attached to the fixing member 4.

The subject stage 5 on which the subject can be placed, and the cover unit 6 to protect the first grating 21, the second grading 22, and the radiation detector 23 (see later described FIG. 4) are provided downstream of the ray source grating 20 in the radiation irradiating direction (in other words, z-direction). Although illustration is omitted, a holding apparatus can be positioned on the subject table 5, or a holding apparatus can be provided in the subject table 5 to hold the subject with the holding apparatus and fix the position of the subject or the angle with respect to the radiation irradiating direction.

As shown in FIG. 4, the first grating 21, the second grating 22, the radiation detector 23, etc. is positioned in the cover unit 6. As described above, the interval of the first grating 21 and the second grating 22 is adjusted so that the second grating 22 is positioned in a position where a self-image is focused at a certain interval from the first grating 21 in the z-direction with the radiation irradiated from the radiation source 2 and passing through the first grating 21.

The radiation detector 23 is positioned directly below the second grating 22, and the moire image Mo generated on the second grating 22 is captured with the radiation detector 23. Although illustration is omitted, the radiation detector (FPD) 23 is composed of conversion elements which generate electric signals according to the irradiated radiation positioned two-dimensionally (matrix shape). The electric signal generated by the conversion element is read as the image signal to capture the moire image Mo as the image signal of each conversion element.

When the X-ray Talbot capturing apparatus 1 captures a plurality of moire images Mo using the fringe scanning method, the relative position between the first grating 21 and the second grating 22 is shifted in the x-axis direction shown in FIG. 4 (direction orthogonal to the extending direction (y-axis direction) of the slit S) to capture the plurality of moire images Mo. Therefore, a moving device, etc. (not shown) is provided to shift the relative position between the first grating 21 and the second grating 22 in the x-axis direction. When the X-ray Talbot capturing apparatus 1 captures one moire image Mo and the differential phase image is reconstructed and generated by Fourier transform, the moving device, etc. does not need to be provided.

Although illustration is omitted, the moire image Mo captured with the X-ray Talbot capturing apparatus 1 is transmitted to the controller or the image processing apparatus. The controller or the image processing apparatus reconstructs and generates the absorption image and the differential phase image based on one or a plurality of moire images captured by the radiation detector 23.

[Bent Configuration of Grating]

Next, the configuration to bend each grating (ray source grating 20, first grating 21, second grating 22) in the X-ray Talbot capturing apparatus 1 of the present embodiment is described in detail. FIG. 2 and FIG. 4 show the first grating 21, etc. in a plane shape. However, actually, according to the present embodiment, the gratings 20, 21, and 22 are bent in an arc shape with a point of the radiation source 2 as the center (for example, focus of the radiation source 2 or exit of the radiation source 2, both are not shown) so that the radiation enters the radiation entering surface R in the normal direction in any portion of the radiation entering surface R of the gratings 20, 21, and 22. The first grating 21 is described below as an example, but the same can be said for when the ray source grating 20 or the second grating 22 is bent.

Figure 5A:
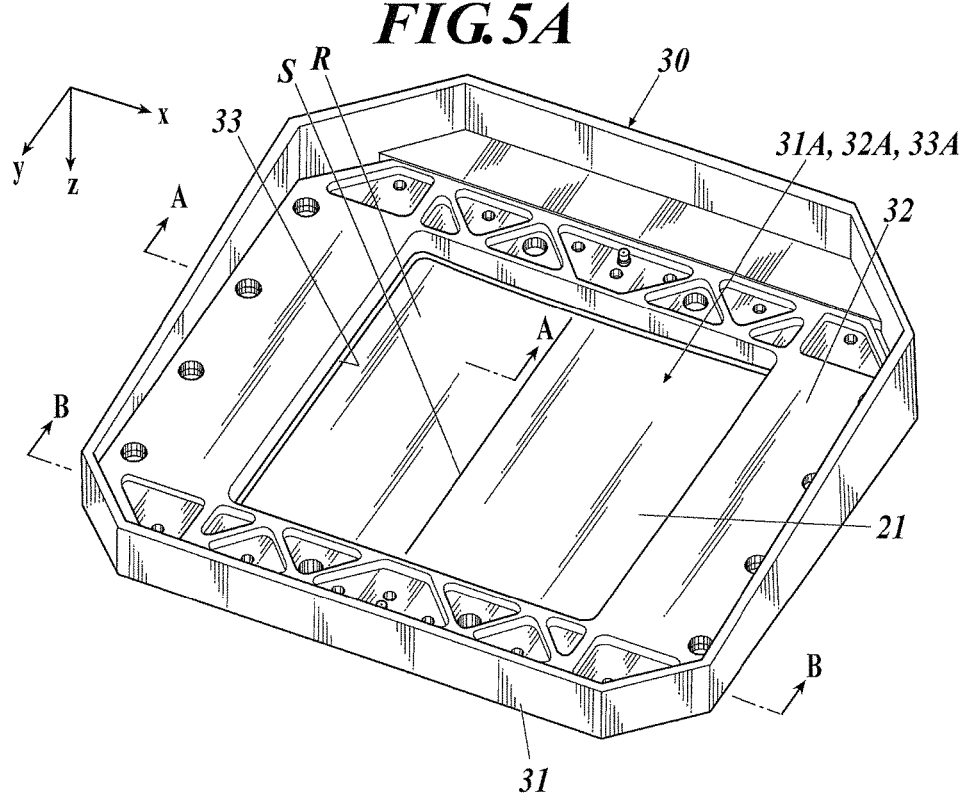
FIG. 5A is a perspective view showing the first grating attached to a holder.
Figure 5B:
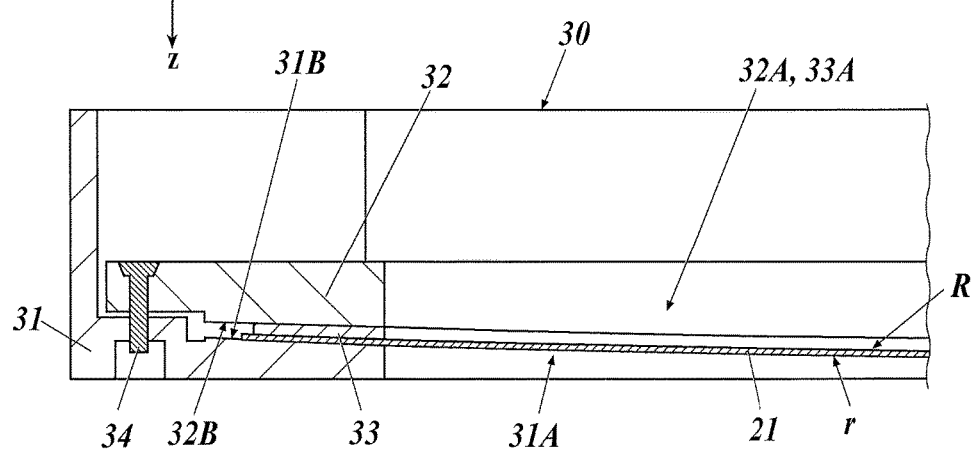
FIG. 5B is a cross-sectional view along line A-A shown in FIG. 5A.
Figure 6:
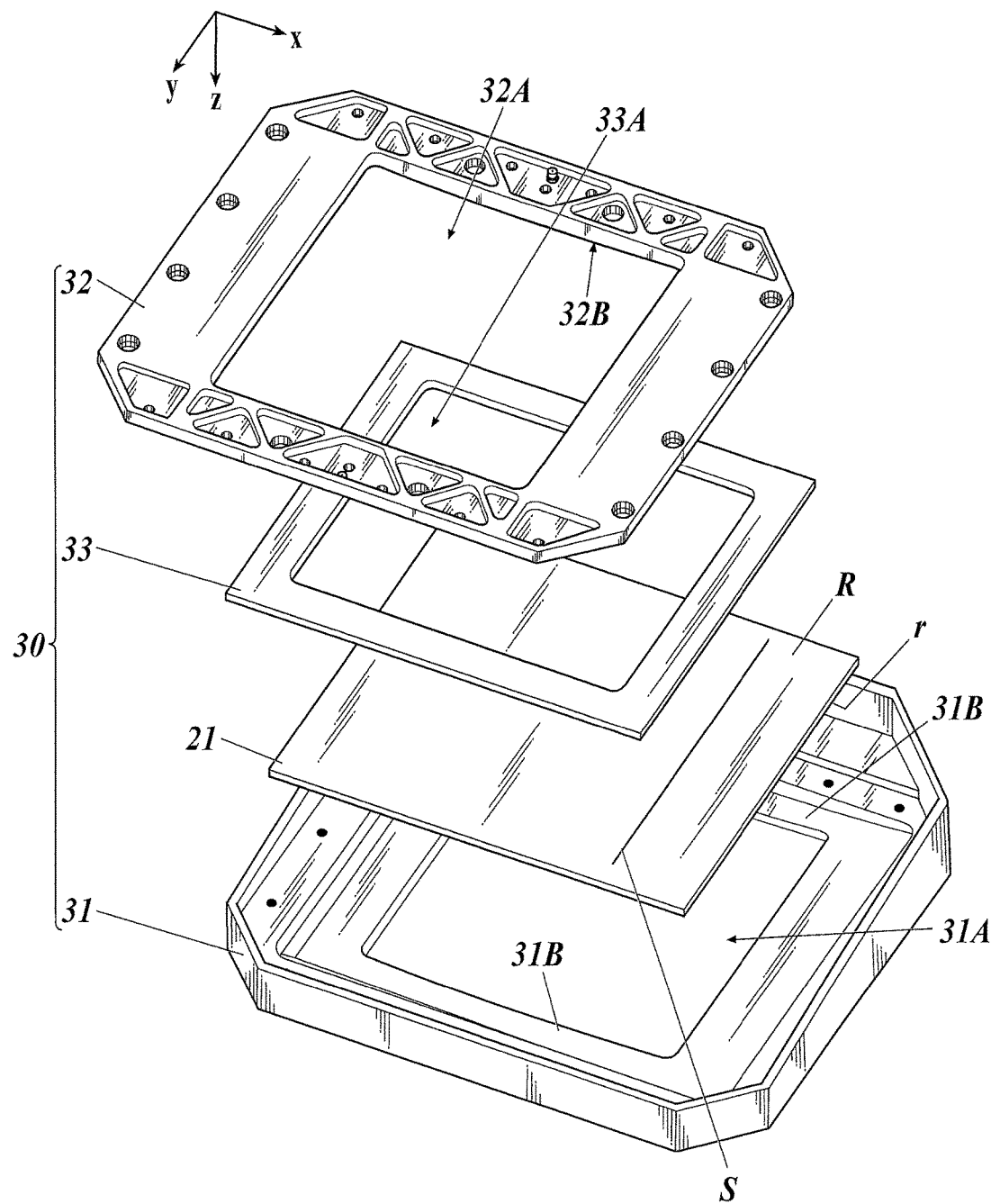
FIG. 6 is an exploded view of the holder.

As shown in FIG. 5A, FIG. 5B, and FIG. 6, the first grating 21 is held in the holder 30 in the bent state. The holder 30 includes a receiving unit 31, a pressing unit 32, and an elastic member 33. FIG. 5A is a perspective view showing the first grating 21 attached to the holder 30, and FIG. 5B is a cross-sectional view along line A-A in FIG. 5A. FIG. 6 is an exploded view of the holder 30.

According to the present embodiment, each grating such as the first grating 21 is formed with one silicon wafer, etc. The receiving unit 31 and the pressing unit 32 of the holder 30 is formed with aluminum, iron, etc. from the viewpoint of hardness, ease of processing, cost, etc., however, the grating and the holder 30 can be applied to the present invention regardless of the material. The radiation is irradiated from the upper side to the lower side (z-direction) in FIG. 5A, FIG. 5B, and FIG. 6.

According to the description below, the upper side of the diagram, in other words, the upstream side of the irradiating direction of radiation is described as upper side or top, and the lower side of the diagram, in other words, the downstream side of the irradiating direction of radiation is described as lower side or bottom. Nevertheless, as described above, for example, when the radiation is emitted in a horizontal direction from the radiation source 2 of the X-ray Talbot capturing apparatus 1 to capture the moire image Mo, the upstream side and the downstream side of the irradiating direction of the radiation becomes a horizontal direction (left and right direction).

Further, FIG. 5A and FIG. 6 show only one representative slit S in the first grating 21 and the slit S is omitted in FIG. 5B. However, as described above, a plurality of slits S are provided in the first grating 21.

Basically, in the present embodiment, the receiving unit 31 of the holder 30 is positioned on the lower side of the first grating 21 (in other words, the radiation emitting surface r side of the first grating 21), the pressing unit 32 of the holder 30 is positioned on the upper side of the first grating 21 (in other words, the radiation entering surface R side of the first grating 21), and the periphery of the first grating 21 is held between the receiving unit 31 and the pressing unit 32 of the holder 30 in the horizontal direction (top and bottom direction).

Then, as shown in FIG. 5B, according to the present embodiment, the receiving unit 31 and the pressing unit 32 of the holder 30 are connected with screws 34 throughout the whole circle of the periphery, and the first grating 21 is held between the receiving unit 31 and the pressing unit 32. When the receiving unit 31 and the pressing unit 32 of the holder 30 are connected with the screws 34 at only a predetermined position of the periphery, the first grating 21 may not be accurately bent at the portions which are not connected with the screw 34 due to the high stiffness of the first grating 21. According to the present embodiment, the receiving unit 31 and the pressing unit 32 of the holder 30 are connected with screws 34 throughout the whole circle of the periphery. Therefore, it is possible to accurately prevent problems as described above, and to hold the first grating 21 (and the later-described elastic member 33) with an even strength between the receiving unit 31 and the pressing unit 32.

According to the present embodiment, in the holder 30, the receiving surface 31B of the receiving unit 31 pressing the first grating 21 (in other words, the portion of the receiving surface 31B in a frame shape other than a later-described opening 31A of the receiving unit 31 of the holder 30) has a curve with a predetermined curvature. Moreover, the pressing surface 32B of the pressing unit 32 facing the receiving surface 31B of the receiving unit 31 receiving the first grating 21 and the elastic member 33 with the first grating 21 and the elastic member 33 in between (in other words, the portion of the pressing surface 32B in a frame shape other than a later-described opening 32A of the pressing unit 32 of the holder 30) has a curve with a predetermined curvature. In other words, according to the present embodiment, the receiving surface 31B of the receiving unit 31 of the holder 30 and the pressing surface 32B of the pressing unit 32 are bent in an arc shape with the above-described point of the radiation source 2 (for example, focus of the radiation source 2 or the exit of the radiation source 2, both are not shown) as the center.

Then, when the first grating 21 is held with the holder 30, the first grating 21 is held between the curved receiving surface 31B of the receiving unit 31 provided in the downstream side of the irradiating direction of the radiation (bottom side of the figure) and the curved pressing surface 32B of the pressing unit 32 provided on the upstream side of the irradiating direction of the radiation (top side of the figure). With this, as described above, the first grating 21 is bent in an arc shape with the above-described point of the radiation source 2 (for example, focus of the radiation source 2 or the exit of the radiation source 2, both are not shown) as the center.

When the receiving unit 31 and the pressing unit of the holder 30 are made, as described above, the receiving surface 31B of the receiving unit 31 and the pressing surface 32B of the pressing unit 32 are made bent in an arc shape with the above-described point of the radiation source 2 (for example, focus of the radiation source 2 or the exit of the radiation source 2, both are not shown) as the center. However, since there is a limit to the accuracy of processing by machine, actually, the receiving surface 31B of the receiving unit 31 and the pressing surface 32B of the pressing unit 32 are not made in an arc shape with the point of the radiation source 2 as the center without any error. Therefore, the present application describing an "arc shape with the point of the radiation source 2 as the center", includes error of processing by the machine.

According to the present embodiment, the elastic member 33 is positioned between the radiation entering surface R of the first grating 21 and the pressing surface 32B of the pressing unit 32 of the holder 30. FIG. 5A, FIG. 5B and FIG. 6 show the elastic member 33 positioned between the first grating 21 and the pressing unit 32. Alternatively, as described in the later-described FIG. 9A and FIG. 9B, the elastic member 33 can be positioned between the radiation exiting surface r of the first grating 21 and the receiving surface 31B of the receiving unit 31 of the holder 30.

The openings 31A, 32A, and 33A are each provided in the receiving unit 31 and the pressing unit 32 of the holder 30 and the elastic member 33 so as not to block the radiation irradiated to the first grating 21. Here, when the radiation irradiated to the first grating 21 hits the receiving unit 31 or the pressing unit 32 of the holder 30 and reflects or scatters causing bad effects, for example, the receiving unit 31 and the pressing unit 32 can be formed from metal which does not pass radiation, for example, lead, or a metallic layer such as lead, can be provided in the portion of the surface of the receiving unit 31 which may be hit by the radiation.

[Operation]

Next, the operation of the X-ray Talbot capturing apparatus 1 of the present embodiment, specifically, the grating portions such as the ray source grating 20, the first grating 21, and the second grating 22 are described below.

Below, the first grating 21 is described as an example, but the same description applies for the ray source grating 20 and the second grating 22. Moreover, the example of positioning the elastic member 33 between the first grating 21 and the pressing unit 32 of the holder 30 is described, but the same description applies for when the elastic member 33 is positioned between the radiation exiting surface r of the first grating 21 and the receiving surface 31B of the receiving unit 31.

As described above, diffraction grating described in Japanese Patent Application Laid-Open Publication No. 2012-13530 is formed by aligning a plurality of small gratings placed between a first and second supporting substrate to form one bonded grating plate, and the bonded grating plate is bent by placing the bonded grating plate between a concave surface stage and a convex surface stage. Therefore, the bonded grating plate corresponds to the first grating (ray source grating 20, second grating 22) of the present embodiment and the concave surface stage and the convex surface stage corresponds to the receiving unit 31 and the pressing unit 32 of the holder 30 of the present embodiment.

The conventional grating portion including the diffraction grating described in Japanese Patent Application Laid-Open Publication No. 2012-13530 is not provided with the elastic member 33 of the present embodiment between the first grating 21 (bonded grating plate in Japanese Patent Application Laid-Open Publication No. 2012-13530), and the receiving unit 31 and the pressing unit 32 of the holder 30 (concave surface stage and convex surface stage in Japanese Patent Application Laid-Open Publication No. 2012-13530).

As described above, even if the receiving unit 31 and the pressing unit 32 of the holder 30 are made so that the receiving surface 31B of the receiving unit 31 and the pressing surface 32B of the pressing unit 32 are shaped in an arc shape with the point of the radiation source 2 as the center, since there is a limit to the accuracy of processing by machine, actually, the center of the arc of the receiving surface 31B of the receiving unit 31 and the pressing surface 32B of the pressing unit 32 is not always the exact same point of the radiation source 2.

Figure 7A:
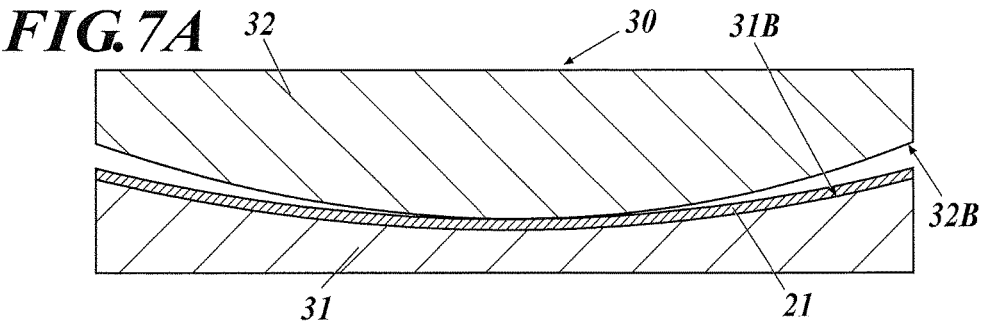
FIG. 7A is a schematic cross sectional view along line B-B shown in FIG. 5A when an elastic member is not provided.

Therefore, when the elastic member 33 as described in the present embodiment is not provided between the first grating 21 (bonded grating plate) and the receiving unit 31 and the pressing unit 32 of the holder 30 (concave surface stage and convex surface stage), if the receiving unit 31 and the pressing unit 32 (concave surface stage and convex surface stage) are connected with screws 34 with the first grating (bonded grating plate) in between (see FIG. 5B), as shown in FIG. 7A, for example, the center (not shown) of the arc formed in the pressing surface 32B of the pressing unit 32 (convex surface stage) may be closer to the holder 30 than the center (not shown) of the arc formed in the receiving surface 31B of the receiving unit 31 (concave surface stage). In this case, the first grating 21 (bonded grating plate) matches with the pressing unit 32 (convex surface stage) at a point in a position at substantially the center.

Figure 7B:
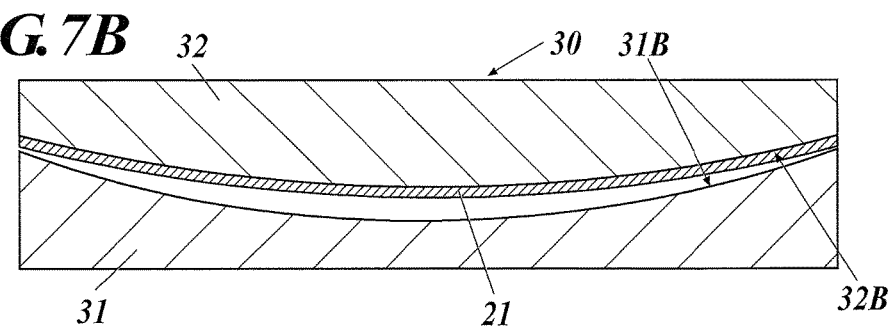
FIG. 7B is a schematic cross sectional view along line B-B shown in FIG. 5A when the elastic member is not provided.

As shown in FIG. 7B, the center (not shown) of the arc formed in the pressing surface 32B of the pressing unit 32 (convex surface stage) of the holder 30 may be farther from the holder 30 than the center (not shown) of the arc formed in the receiving surface 31B of the receiving unit 31 (concave surface stage). In this case, the first grating 21 (bonded grating plate) matches with the receiving unit 31 (concave surface stage) at points in positions at both edges. When the first grating 21 is formed with a material with stiffness such as a silicon wafer, etc., as shown in FIG. 7B, the first grating 21 follows the pressing surface 32B of the pressing unit 32 (convex surface stage).

FIG. 7A and FIG. 7B are schematic cross-sectional diagrams along line B-B of FIG. 5A when the elastic member 33 is not provided, and the later-described FIG. 8A, FIG. 8B, FIG. 9A, and FIG. 9B are schematic cross-sectional diagrams along line B-B of FIG. 5A when the elastic member 33 is provided as in the present embodiment.

In FIG. 7A and FIG. 7B, and the later-described FIG. 8A, FIG. 8B, FIG. 9A, and FIG. 9B for the purpose of ease of understanding, the difference of the curvature and the difference of the curvature radius of the arc between the receiving unit 31 (concave surface stage) and the pressing unit 32 (convex surface stage) of the holder 30 is emphasized than the actual difference. Actually, there is hardly any difference in the position of the center (not shown) of the arc formed in the above. However, a slight difference occurs in the position of the center due to the limit of accuracy of processing by machine. Therefore, as shown in FIG. 7A and FIG. 7B, the first grating 21 (bonded grating plate) is matched at the point with the receiving unit 31 (concave surface stage) and the pressing unit 32 (convex surface stage).

As described above, when the first grating 21 (bonded grating plate) is matched at the point with the receiving unit 31 and the pressing unit 32 of the holder 30 (concave surface stage and convex surface stage), the stress is concentrated in the portion of the matching point. This may cause damage to the first grating 21 such as the first grating 21 breaking at the portion of the matching point similar to the method shown in FIG. 6 of Japanese Patent Application Laid-Open Publication No. 2007-206075.

Figure 8A:
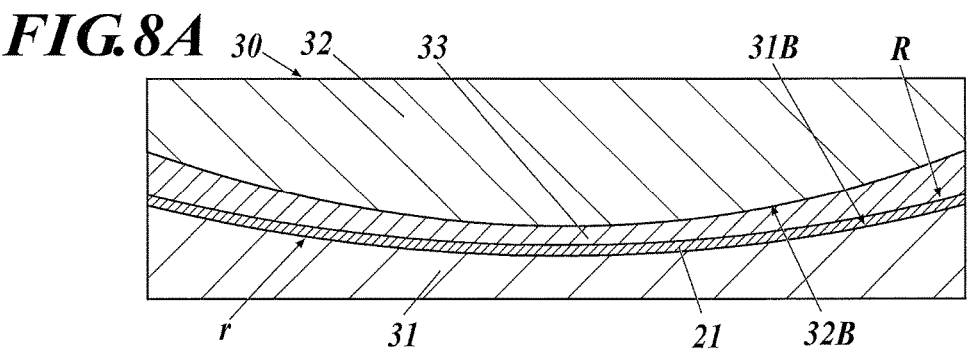
FIG. 8A is a schematic cross sectional view along line B-B shown in FIG. 5A when the elastic member is provided between the first grating and a pressing unit of the holder.
Figure 8B:
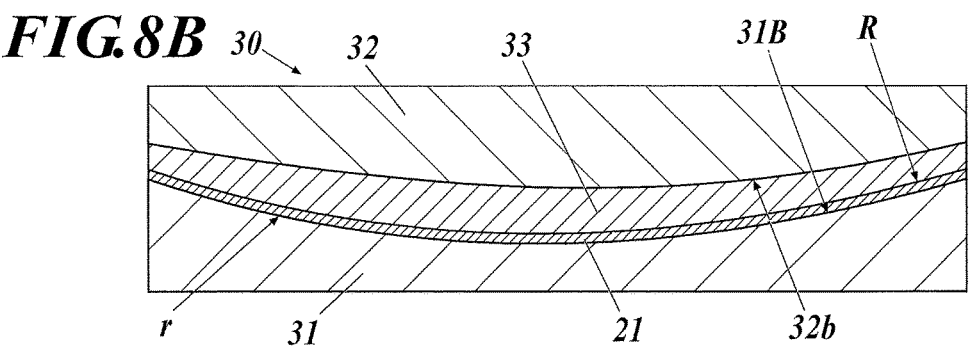
FIG. 8B is a schematic cross sectional view along line B-B shown in FIG. 5A when the elastic member is provided between the first grating and the pressing unit of the holder.

According to the present embodiment, the elastic member 33 is positioned between the radiation entering surface R of the first grating 21 and the pressing surface 32B of the pressing unit 32 of the holder 30 resulting in a state as shown in FIG. 8A and FIG. 8B. FIG. 8A and FIG. 8B respectively correspond to FIG. 7A and FIG. 7B, and the center (not shown) of the arc formed in the pressing surface 32B of the pressing unit 32 of the holder 30 may be closer to the holder 30 (FIG. 8A) or farther from the holder 30 than (FIG. 8B) the center (no shown) of the arc formed in the receiving surface 31B of the receiving unit 31. The elastic member 33 is positioned between the radiation entering surface R of the first grating 21 and the pressing surface 32B of the pressing unit 32.

Since the elastic member 33 is positioned between the radiation entering surface R of the first grating 21 and the pressing surface 32B of the pressing unit 32 of the holder 30, even if there is a slight difference between the position of the center (not shown) of the arc formed in the receiving surface 31B of the receiving unit 31 and the position of the center (not shown) of the arc formed in the pressing surface 32B of the pressing unit 32, as shown in FIG. 8A and FIG. 8B, the elastic member 33 suitably shrinks (that is, crushed) by the pressing force of the pressing unit 32, and the first grating 21 is entirely pressed to the receiving surface 31B of the receiving unit 31. In other words, instead of being matched at the point, the periphery of the first grating 21 (see FIG. 6) has surface contact with the receiving surface 31B of the receiving unit 31. Therefore, in the first grating 21, the entire radiation entering surface R is pressed against the elastic member 33, and the entire radiation exiting surface r is pressed against the receiving surface 31B of the receiving unit 31.

Therefore, since the elastic member 33 is positioned between the radiation entering surface R of the first grating 21 and the pressing surface 32B of the pressing unit 32 of the holder 30, it is possible to accurately prevent the first grating 21 being matched at the point with the pressing unit 32 of the holder 30. Moreover, the first grating 21 has surface contact with the receiving surface 31B of the receiving unit 31 and the elastic member 33 due to the pressing force from the pressing surface 32B of the pressing unit 32. Therefore, stress concentration as in matching at the point does not occur, and it is possible to accurately prevent damage such as the first grating 21 breaking.

When the curvature of the receiving surface 31B of the receiving unit 31 of the holder 30 to which the first grating 21 is pressed is processed in advance to be a certain value, the first grating 21 having surface contact with the receiving surface 31B of the receiving unit 31 is bent at the same curvature (that is, the certain curvature) as the curvature of the receiving surface 31B of the receiving unit 31. In other words, the first grating 21 is bent in an arc with the center being the same point as the center (not shown) (that is, the above-described point of the radiation source 2) of the arc formed in the receiving surface 31B of the receiving unit 31.

Figure 9A:
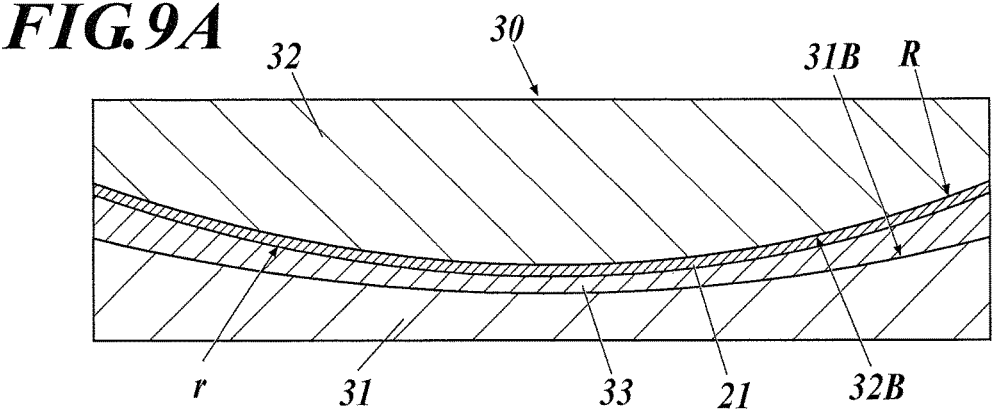
FIG. 9A is a schematic cross sectional view along line B-B shown in FIG. 5A when the elastic member is provided between the first grating and a receiving unit of the holder.
Figure 9B:
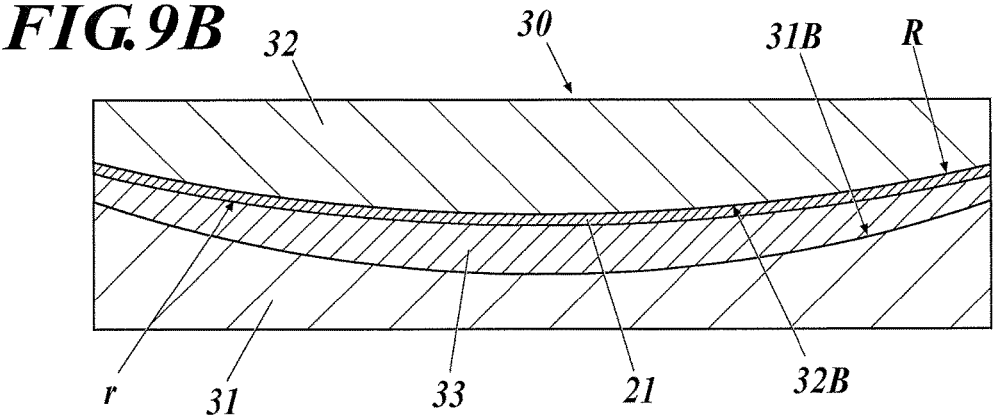
FIG. 9B is a schematic cross sectional view along line B-B shown in FIG. 5A when the elastic member is provided between the first grating and the receiving unit of the holder.

For example, as shown in FIG. 9A and FIG. 9B, the elastic member 33 can be positioned between the radiation exiting surface r of the first grating 21 and the receiving surface 31B of the receiving unit 31 of the holder 30. FIG. 9A and FIG. 9B respectively correspond to FIG. 7A and FIG. 7B, and the center (not shown) of the arc formed in the pressing surface 32B of the pressing unit 32 may be closer to (FIG. 9A) or farther from (FIG. 9B) the holder 30 than the center (not shown) of the arc formed in the receiving surface 31B of the receiving unit 31. The elastic member 33 is positioned between the radiation exiting surface r of the first grating 21 and the receiving surface 31B of the receiving unit 31.

When the elastic member 33 is positioned between the radiation exiting surface r of the first grating 21 and the receiving surface 31B of the receiving unit 31 of the holder 30, even if there is a slight difference between the position of the center (not shown) of the arc formed in the receiving surface 31B of the receiving unit 31, and the position of the center (not shown) of the arc formed in the pressing surface 32B of the pressing unit 32, as shown in FIG. 9A and FIG. 9B, the elastic member 33 suitably shrinks with the pressing force of the receiving unit 31. With this, the first grating 21 is entirely pressed against the pressing surface 32B of the pressing unit 32. Therefore, in the first grating 21, the entire radiation exiting surface r is pressed against the elastic member 33, and the entire radiation entering surface R is pressed against the pressing surface 32B of the pressing unit 32.

Therefore, since the elastic member 33 is positioned between the radiation exiting surface r of the first grating 21 and the receiving surface 31B of the receiving unit 31 of the holder 30, it is possible to accurately prevent the first grating 21 being matched at the point with the receiving unit 31 and the pressing unit 32. Moreover, the first grating 21 has surface contact with the pressing surface 32B of the pressing unit 32 and the elastic member 33 due to the pressing force from the receiving surface 31B of the receiving unit 31. Therefore, stress concentration as in matching at the point does not occur, and it is possible to accurately prevent damage such as the first grating 21 breaking.

When the curvature of the pressing surface 32B of the pressing unit 32 of the holder 30 to which the first grating 21 is pressed is processed in advance to be a certain value, the first grating 21 having surface contact with the pressing surface 32B of the pressing unit 32 is bent at the same curvature (that is, the certain curvature) as the curvature of the pressing surface 32B of the pressing unit 32. In other words, the first grating 21 is bent in an arc with the center being the same point as the center (not shown) (that is, the above-described point of the radiation source 2) of the arc formed in the pressing surface 32B of the pressing unit 32.

[Effect]

As described above, according to the X-ray Talbot capturing apparatus 1 of the present embodiment, when the first grating 21, etc. (that is, the ray source grating 20, the first grating 21, and the second grating 22) is held with the holder 30, the elastic member 33 is positioned between the radiation entering surface R of the first grating 21, etc. and the pressing surface 32B of the pressing unit 32 or the radiation exiting surface r of the first grating, etc. and the receiving surface 31B of the receiving unit 31.

Therefore, even if the position of the center (not shown) of the arc formed in the receiving surface 31B of the receiving unit 31 of the holder 30 is different from the position of the center (not shown) of the arc formed in the pressing surface 32B of the pressing unit 32 due to the limit of accuracy of processing by machine, the elastic member 33 suitably shrinks with the pressing force of the pressing unit 32 and the receiving unit 31. With this, the first grating 21 can be entirely pressed against the receiving surface 31B of the receiving unit 31 and the pressing surface 32B of the pressing unit 32, that is, the first grating 21 has surface contact.

As described above, in the X-ray Talbot capturing apparatus 1 of the present embodiment, stress concentration such as matching at the point does not occur when the holder 30 holds the first grating 21, etc. Therefore, it is possible to accurately prevent damage occurring, such as the first grating 21, etc. breaking.

The curvature of the receiving surface 31B of the receiving unit 31 of the holder 30 and the pressing surface 32B of the pressing unit 32 is processed in advance to be a certain curvature, and the first grating 21, etc. in surface contact with the above is bent to have a certain curvature. Therefore, the first grating 21, etc. can be accurately bent in an arc with the point of the radiation source 2 (see FIG. 1 and FIG. 2) of the radiation source 2 as the center.

Therefore, since the radiation enters the radiation entering surface R in the normal direction in any portion of the radiation entering surface R of the first grating 21, etc., it is possible to accurately prevent problems such as vignetting, and the radiation can be accurately passed. In the X-ray Talbot capturing apparatus 1 of the present embodiment, the openings 31A, 32A, and 33A are respectively provided in the receiving unit 31 and the pressing unit 32 of the holder 30 and the elastic member 33 so that the radiation irradiated to the first grating 21, etc. is not blocked. The radiation is not reflected or scattered by the receiving unit 31, the pressing unit 32 or the elastic member 33, and the radiation can pass accurately.

According to the present embodiment, as described above, although there is a limit to the accuracy of processing by machine, forming the receiving unit 31 and the pressing unit 32 so that the position of the center of the arc formed in the receiving surface 31B of the receiving unit 31 of the holder 30 and the position of the center of the arc formed in the pressing surface 32B of the pressing unit 32 are basically the same point of the radiation source 2 (that is, positions which are not shown such as the focus or the exit of the radiation source 2).

However, as described above, for example, as shown in FIG. 8A and FIG. 8B, even if there is a difference between the position of the center (not shown) of the arc formed in the receiving surface 31B of the receiving unit 31 of the holder 30 and the position of the center (not shown) of the arc formed in the pressing surface 32B of the pressing unit 32, the elastic member 33 positioned between the radiation entering surface R of the first grating 21, etc. and the pressing surface 32B of the pressing unit 32 of the holder 30 shrinks (that is, crushed) with the pressing force of the pressing unit 32 and the entire first grating 21 is pressed against the receiving surface 31B of the receiving unit 31. With the elastic member 33, the first grating 21, etc. is not separated from the receiving surface 31B of the receiving unit 31, and has surface contact with the receiving surface 31B of the receiving unit 31. Therefore, it is possible to accurately bend the first grating 21, etc. in an arc (that is, a predetermined curvature) with the center at the same point as the center (not shown) (that is, the above-described point of the radiation source 2) of the arc formed in the receiving surface 31B of the receiving unit 31 of the holder 30.

Moreover, for example, as shown in FIG. 9A and FIG. 9B, even if there is a difference between the position of the center (not shown) of the arc formed in the receiving surface 31B of the receiving unit 31 of the holder 30 and the position of the center (not shown) of the arc formed in the pressing surface 32B of the pressing unit 32, the elastic member 33 positioned between the radiation exiting surface r of the first grating 21, etc. and the receiving surface 31B of the receiving unit 31 of the holder 30 shrinks (that is, crushed) with the pressing force of the receiving unit 31 and the pressing unit 32 and the entire first grating 21 is pressed against the pressing surface 32B of the pressing unit 32. With the elastic member 33, the first grating 21, etc. is not separated from the pressing surface 32B of the pressing unit 32, and has surface contact with the pressing surface 31B of the receiving unit. Therefore, it is possible to accurately bend the first grating 21, etc. in an arc (that is, a predetermined curvature) with the center at the same point as the center (not shown) (that is, the above-described point of the radiation source 2) of the arc formed in the pressing surface 32B of the pressing unit 32 of the holder 30.

Therefore, the position of the center (not shown) of the arc formed in the receiving surface 31B of the receiving unit 31 of the holder 30 and the position of the center (not shown) of the arc formed in the pressing surface 32B of the pressing surface 32 of the holder 30 can be different as long as the elastic member 33 can suitably shrink (that is, crushed) with the pressing force of the receiving unit 31 and the pressing unit 32 and the first grating 21, etc. can be formed having accurate surface contact without the first grating 21 etc. of the holder 30 being separated from the receiving surface 31B of the receiving unit 31 or the pressing surface 32B of the pressing unit 32.

In this case, when the surface to which the first grating 21, etc. is pressed (that is, the receiving surface 31B of the receiving unit 31 of the holder 30 (in FIG. 8A and FIG. 8B) or the pressing surface 32B of the pressing unit 32 of the holder 30 (in FIG. 8A and FIG. 8B)) with the elastic member 33 is formed bent in an arc shape with the point of the radiation source 2 as the center, the first grating 21, etc. is pressed to the surface with the elastic member 33 to be in surface contact. Therefore, the first grating 21, etc. can be suitably bent at the same predetermined curvature.

[Detailed Configuration of Elastic Member]

The configuration described below is preferable to better achieve the above-described effects of the X-ray Talbot capturing apparatus 1.

[Configuration 1]

According to the present embodiment, as described above, the elastic member 33 is suitably crushed by the pressing force of the pressing unit 32 of the holder 30 (in FIG. 8A and FIG. 8B) and the pressing force of the receiving unit 31 (in FIG. 9A and FIG. 9B). With this, the first grating 21 is pressed entirely against the receiving surface 31B of the receiving unit 31 (in FIG. 8A and FIG. 8B) and the pressing surface 32B of the pressing unit 32 (in FIG. 9A and FIG. 9B), that is a surface contact state.

In order to form this state, it is preferable that the thickness of the elastic member 33 is 1.6 mm or more. It is preferable that the crushing margin (that is, amount of change of thickness) of the elastic member 33 is within a range of 0.6 to 0.7 mm when a load of 400 g is applied per 1 cm2.

If the elastic member 33 is too soft, it becomes difficult to press the first grating 21, etc. having high stiffness with pressing force of the elastic member 33. As shown in FIG. 7B, the first grating 21, etc. becomes separated from the receiving surface 31B of the receiving unit 31 of the holder 30, and the first grating 21, etc. cannot be maintained at the predetermined curvature or the predetermined arc. If the elastic member 33 is too hard, the receiving unit 31 and the pressing unit 32 is deformed by the stiffness of the elastic member 33 and the first grating 21, etc. when the receiving unit 31 is connected to the pressing unit 32 with the screws 34 (see FIG. 5B) with the elastic member 33 and the first grating 21, etc. in between. Therefore, the curvature and the arc of the receiving surface 31B of the receiving unit 31 and the pressing surface 32B of the pressing unit 32 (that is, the surface to which the first grating 21, etc. is pressed) are shifted from the predetermined curvature and the predetermined arc.

When the elastic member 33 has a degree of hardness (or flexibility) as described above, it is possible to accurately prevent the above situations, and the first grating 21, etc. can be accurately bent at a suitable curvature by holding the first grating 21, etc. with the holder 30. In other words, the first grating 21 can be accurately bent in an arc with the center at the same point as the center (not shown) (that is, the point of the radiation source 2) of the arc formed in the side having contact (that is, the receiving surface 31B of the receiving unit 31 of the holder 30 or the pressing surface 32B of the pressing unit 32).

[Configuration 2]

Figure 10A:
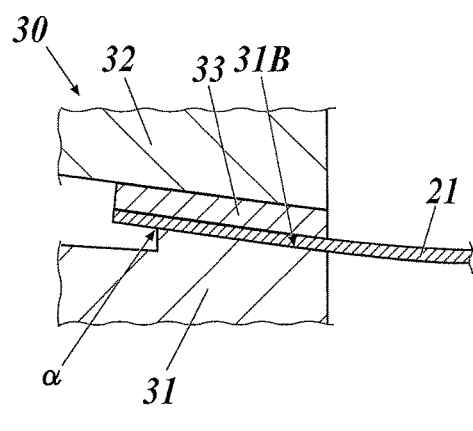
FIG. 10A is a schematic cross sectional view showing a state in which an edge of the elastic member projects outward than a receiving surface of the receiving unit of the holder.

For example, as shown in FIG. 10A, when the elastic member 33 is positioned between the first grating 21, etc. and the pressing member 32 of the holder 30, if the edge of the elastic member 33 is outside the edge α of the receiving surface 31B of the receiving unit 31 in contact with the first grating 21, etc. (that is, in contact without elastic member 33 in between), when the elastic member 33 is pressed with the pressing unit 32, stress concentration occurs in the portion of the edge α of the receiving surface 31B of the receiving unit 31 and damage such as the first grating 21, etc. breaking at this portion may occur.

Figure 10B:
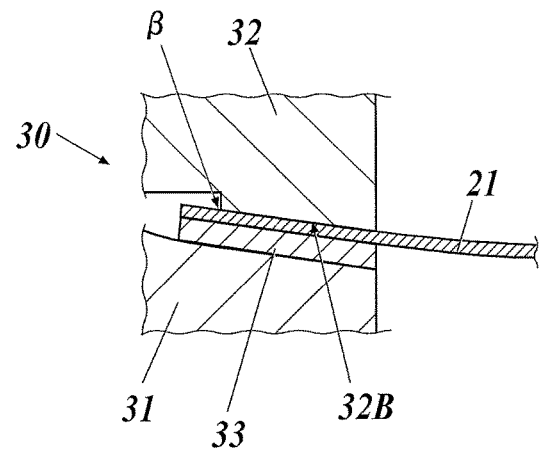
FIG. 10B is a schematic cross sectional view showing a state in which the edge of the elastic member projects outward than an edge of the pressing surface of the pressing unit of the holder.

The same can be said for when the elastic member 33 is positioned between the first grating 21, etc. and the receiving unit 31 of the holder 30. As shown in FIG. 10B, when the edge of the elastic member 33 is outside the edge β of the pressing surface 32B of the pressing unit 32 in contact with the first grating 21, etc., if the receiving unit 31 presses the elastic member 33, the stress concentration occurs in the portion of the edge β of the pressing surface 32B of the pressing unit 32, and damage such as the first grating 21, etc. breaking at this portion may occur.

Therefore, as shown in FIG. 5B, it is preferable that the edge of the elastic member 33 is not outside the edge of the surface (that is, the receiving surface 31B of the receiving unit 31 and the pressing surface 32B of the pressing unit 32) of the holder 30 on the side in contact with the first grating 21, etc. According to such configuration, it is possible to accurately prevent damage such as the first grating 21, etc. breaking at this portion.

[Measure for Deforming of the Holder Due to Temperature]

For example, as described above, the receiving unit 31 and the pressing unit 32 of the holder 30 is formed from aluminum, iron, etc. and the first grating 21, etc. is formed from a silicon wafer, etc. Since the thermal expansion coefficient is different between the silicon wafer and aluminum or iron, when the temperature increases, the degree of deforming of the receiving unit 31 and the pressing unit 32 is different from the degree of deforming of the grating of the first grating 21, etc.

For example, therefore, problems may occur such as not being able to capture the suitable moire image Mo with the X-ray Talbot capturing apparatus 1 due to the shift in position of the first grating 21 in the receiving unit 31.

[Configuration 3]

The thermal expansion coefficient of aluminum is about 23×10-6/K and the thermal expansion coefficient of iron is about 12×10-6/K whereas the thermal expansion coefficient of the silicon wafer is about 3.3×10-6/K. Therefore, the ratio of the thermal expansion coefficient of aluminum or iron to the thermal expansion coefficient of the silicon wafer is about 7 times (Al) or 3.6 times (Fe). When the temperature rises, the difference in the thermal expansion coefficient is considered to be one of the reasons the shift in position of the first grating 21 occurs in the holder 30.

The present inventors found that by forming the receiving unit 31 and the pressing unit 32 of the holder 30 with invar (a type of Fe—Ni alloy, thermal expansion coefficient is about 1.5×10-6/K) which is known to have a small thermal expansion coefficient, and placing the elastic member 33 and the first grating 21, etc. which is formed from the silicon wafer between the above, there is no shift in the position of the first grating 21, etc. in the holder 30 within the range of the rise in temperature in a state under normal use of the X-ray Talbot capturing apparatus 1.

The present inventors also found that when the receiving unit 31 and the pressing unit 32 of the holder 30 and the grating of the first grating 21, etc. are formed with various material with different thermal expansion coefficients, and the temperature is changed, when the absolute value of the difference between the thermal expansion coefficient of the receiving unit 31 and the pressing unit 32 with respect to the thermal expansion coefficient of the grating of the first grating 21, etc. is within the range of 4×10-6/K, the position of the first grating 21, etc. does not shift within the holder 30 and the moire image Mo can be suitably captured with the X-ray Talbot capturing apparatus 1.

According to the findings of the present inventors, in addition to the above configuration 3, the moire image Mo can be suitably captured with the X-ray Talbot capturing apparatus 1 without the position of the first grating 21, etc. shifting in the holder 30 by employing the following configuration.

[Configuration 4]

As described above, it is effective to process the surface of the receiving surface 31B (see FIG. 8A, FIG. 8B) of the receiving unit 31 of the holder 30 and the pressing surface 32B of the pressing unit 32 (see FIG. 9A, FIG. 9B) in contact with the first grating 21, etc. so that the surfaces easily slide such as processing with alumite or fluorine coating.

For example, if such surface processing is not performed, when the temperature rises and the receiving unit 31 and the pressing unit 32 of the holder 30 in contact with the first grating 21, etc., extends in the horizontal direction of the diagram from the state shown in FIG. 8A, FIG. 8B, FIG. 9A, and FIG. 9B, the first grating 21, etc. is pulled by the receiving unit 31 or the pressing unit 32 and moves in the left direction or the right direction. Since the first grating 21, etc. moves as described above, the position of the first grating 21, etc. is shifted in the holder 30.

However, as described above, if the surface is processed so that the surface in contact with the first grating 21, etc. slides easily, even if the temperature rises, and the receiving unit 31 and the pressing unit 32 of the holder 30 in contact with the first grating 21, etc., extends in the horizontal direction of the diagram from the state shown in FIG. 8A, FIG. 8B, FIG. 9A, and FIG. 9B, the first grating 21, etc. is not pulled by the receiving unit 31 or the pressing unit 32 and does not move and stays in the original position.

Therefore, by processing the surface as described above, even if the temperature rises, the position of the first grating 21, etc. shifting in the holder 30 can be prevented, and the moire image Mo can be suitably captured with the X-ray Talbot capturing apparatus 1.

[Configuration 5]

According to the configuration 1, the elastic member 33 is suitably crushed by the pressing force of the pressing unit 32 of the holder 30 (in FIG. 8A and FIG. 8B) and the pressing force of the receiving unit 31 (in FIG. 9A and FIG. 9B), and the first grating 21 suitably contacts the receiving surface 31B of the receiving unit 31 (in FIG. 8A and FIG. 8B) and the pressing surface 32B of the pressing unit 32 (in FIG. 9A and FIG. 9B) by the surface. The suitable hardness (or flexibility) of the elastic member 33 to realize the above is described above.

If the elastic member 33 has suitable hardness (or flexibility), it is known that even if the temperature rises, and the receiving unit 31 and the pressing unit 32 of the holder 30 extends, the elastic member 33 suitably deforms and it is possible to suitably prevent the position of the first grating 21, etc. from shifting in the holder 30.

Figure 11:
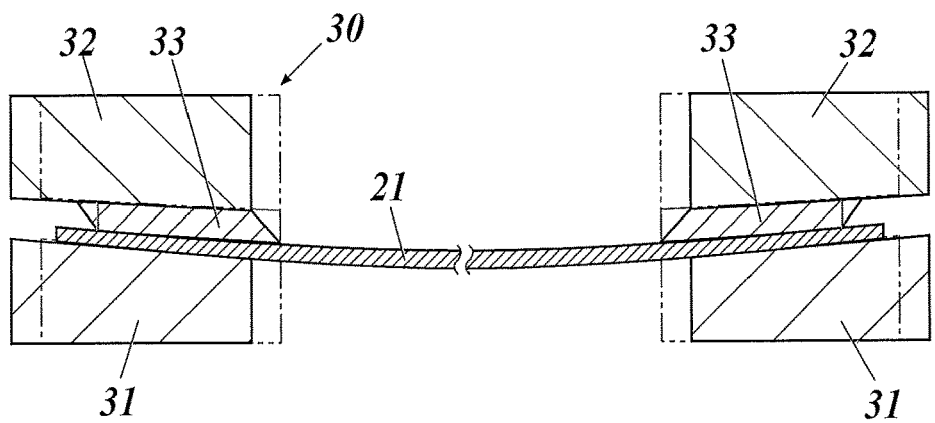
FIG. 11 is a schematic cross sectional view showing a state in which the receiving unit and the pressing unit of the holder extends due to the rise in temperature and the elastic member is deformed.

In other words, when the temperature rises, as shown in FIG. 11, the receiving unit 31 and the pressing unit of the holder 30 extends horizontally from the original state (alternate long and short dash line). If the elastic member 33 is too hard (in other words, hard to deform), the first grating 21, etc. may be pulled in the left direction or the right direction of the drawing when the elastic member 33 extends together with the receiving unit 31 and the pressing unit 32, and the position of the first grating 21, etc. may be shifted in the holder 30.

However, if the elastic member 33 has a suitable hardness (or flexibility), as shown in FIG. 11, the surface of the elastic member 33 in contact with the pressing unit 32 of the holder 30 (or the receiving unit 31 in FIG. 9A and FIG. 9B), moves horizontally pulled by the pressing unit 32 extending horizontally, and the elastic member 33 is deformed.

Since the elastic member 33 is deformed symmetrically horizontally, (that is, for example, the left side portion of the elastic member 33 does not deform larger than the right side portion), the first grating 21, etc. is pulled evenly (in other words, with the same force) in the horizontal direction of the diagram. Therefore, the first grating 21, etc. does not move in the horizontal direction of the diagram. With this, it is possible to prevent the position of the first grating 21, etc. shifting in the holder 30.

The present inventors found that through research the hardness demanded from the elastic member 33 in order to prevent the position of the first grating 21, etc. from moving in the holder 30 is preferably A15 or less in the durometer hardness (conforming to International Standard ISO7619).

[Configuration 6]

Figure 12A:
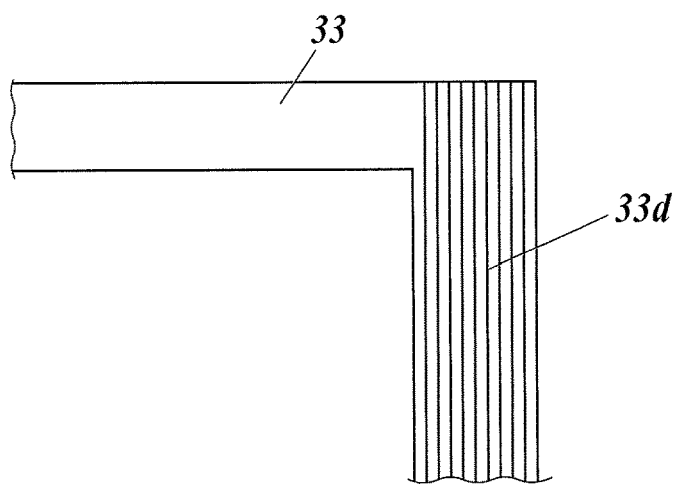
FIG. 12A is a diagram showing a concave unit as a groove formed in the elastic member 33.

As described above, in order to prevent the position of the first grating 21, etc. from shifting in the holder 30, it is preferable that the elastic member 33 deforms flexibly. In order to enable the elastic member 33 to deform easily, for example, the surface of the elastic member 33 in contact with the pressing unit 32 of the holder 30 (or the receiving unit 31 in FIG. 9A and FIG. 9B) has a concave unit 33*d* in a predetermined shape such as a groove as shown in FIG. 12A or a circle as shown in FIG. 12B.

Figure 12B:
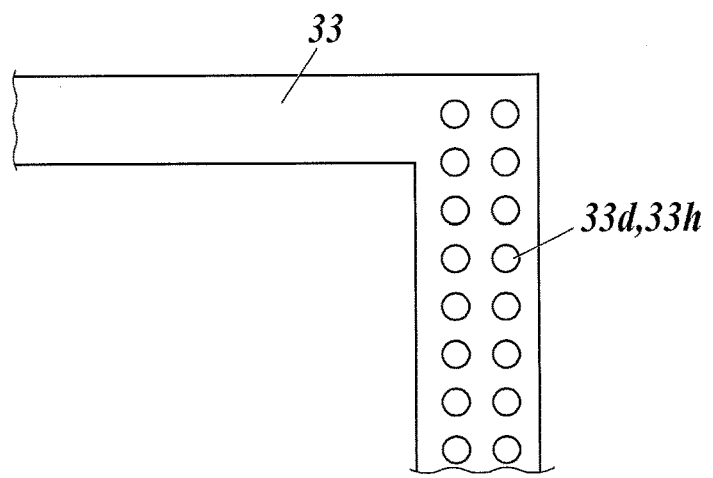
FIG. 12B is a diagram showing a concave unit or hole in a predetermined shape such as a circle formed in the elastic member 33.

Alternatively, the concave unit formed in a predetermined shape such as a circle as shown in FIG. 12B can be formed as a through hole 33*h*. Then, as shown in FIG. 12B, the concave unit 33*d* with the predetermined shape and the hole 33*h* can be formed regularly or can be formed randomly. In FIG. 12A and FIG. 12B, the groove shaped concave unit 33*d*, the predetermined shape concave unit 33*d* and the hole 33*h* are formed only in a predetermined side (that is, the side parallel to the slit S (see FIG. 6) of the first grating 21, etc.) of the elastic member 33. Alternatively, the above can be provided in all sides of the elastic member 33.

According to the above configuration, the elastic member 33 easily deforms due to the concave unit 33*d* and the hole 33*h*. Therefore, even if the temperature rises and the receiving unit 31 and the pressing unit 32 of the holder 30 extends, the elastic member 33 suitably deforms, the first grating 21, etc. is pulled evenly, and the first grating 21, etc. does not move. With this, it is possible to accurately prevent the position of the first grating 21, etc. from moving in the holder 30.

According to the above configuration, when the hardness of the elastic member 33 is larger than the durometer hardness A15, by accurately forming the concave unit 33*d* and the hole 33*h* in the elastic member 33, it is possible to accurately prevent the position of the first grating 21, etc. from moving in the holder 30.

[Configuration to Prevent Deforming of the First Grating, Etc. Due to Temperature]

Figure 13A:
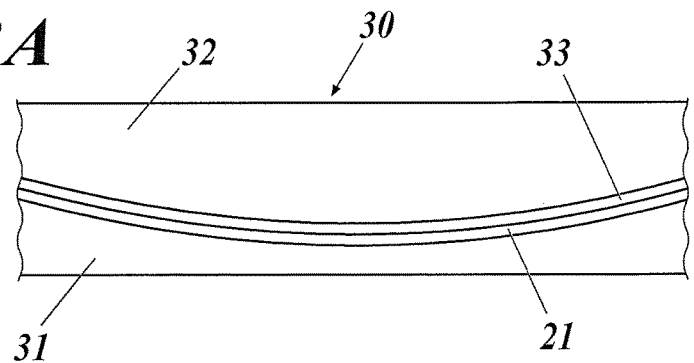
FIG. 13A is a diagram showing the receiving unit and the pressing unit of the holder in an original state before extending.
Figure 13B:
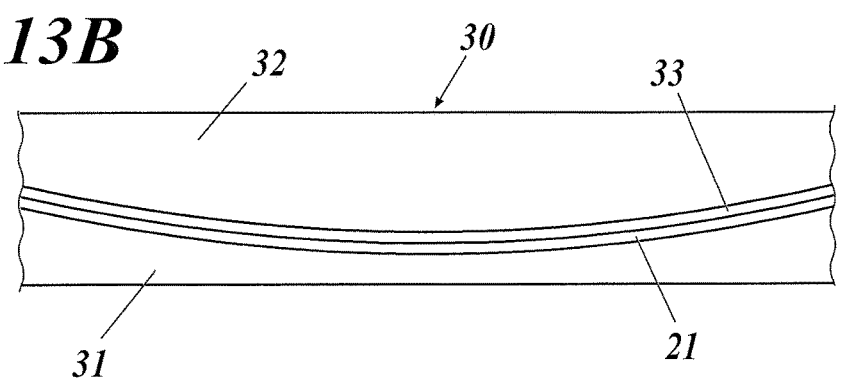
FIG. 13B is a diagram showing a state in which the receiving unit and the pressing unit of the holder extends and a curvature of the first grating, etc. becomes small.

For example, when the temperature rises and the receiving unit 31 and the pressing unit 32 of the holder 30 extend from the state shown in FIG. 13A, as shown in FIG. 13B, the first grating 21, etc. held between the receiving unit 31 and the pressing unit 32 may change and the curvature may become smaller than the original state shown in FIG. 13A (in other words, the curvature radius becomes larger).

Then, when the curvature of the first grating 21, etc. changes, the radiation does not enter the curved first grating 21, etc. in the normal direction, and the problem of vigletting may occur. In FIG. 13A and FIG. 13B and the later described FIG. 14A and FIG. 14B, the deforming and the bending of the receiving unit 31 and the pressing unit 32 of the holder 30 is emphasized more than the actual state.

In order to prevent the curvature of the first grating 21, etc. from changing when the temperature rises and the receiving unit 31 and the pressing unit 32 of the holder 30 extends, the receiving unit 31 can be made from a material including a thermal expansion coefficient larger than the thermal expansion coefficient of the pressing unit.

Figure 14A:
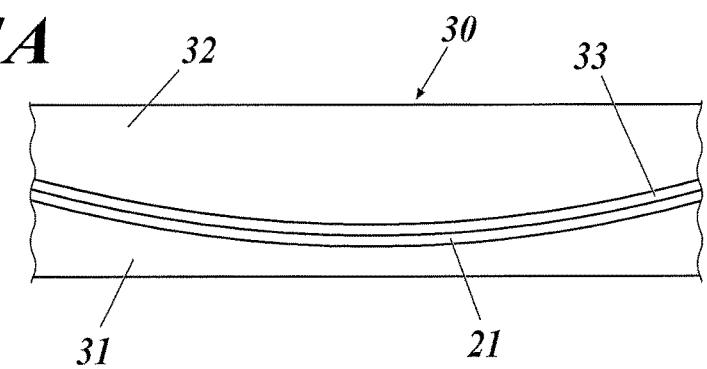
FIG. 14A is a diagram showing the receiving unit and the pressing unit of the holder in the original state before extending.
Figure 14B:
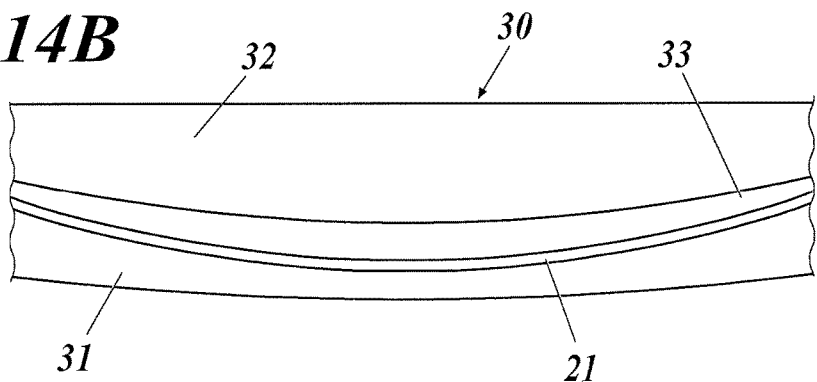
FIG. 14B is a diagram showing a state in which the receiving unit and the pressing unit of the holder extends and the receiving unit sags.

According to the above configuration, when the temperature rises and the receiving unit 31 and the pressing unit 32 of the holder 30 extend from the state shown in FIG. 14A, since the thermal expansion coefficient of the receiving unit 31 is larger than that of the pressing unit 32, the receiving unit 31 sags in a direction separating from the pressing unit 32 as shown in FIG. 14B. Even if the receiving unit 31 sags, the elastic member 33 presses the first grating 21, etc. against the receiving unit 31. Therefore, the curvature of the first grating 21, etc. is the same as the curvature of the sagging receiving unit 31.

The thermal expansion coefficient of the receiving unit 31 of the holder 30 and the thermal expansion coefficient of the pressing unit 32 can be suitably adjusted so that the curvature of the receiving unit 31 sagged due to the rise in temperature is the same curvature as the curvature of the receiving unit 31 before the rise in the temperature (or a curvature so that the problem of vigletting does not occur).

Therefore, according to the above configuration, since the receiving unit 31 suitably sags even if the temperature rises and the receiving unit 31 and the pressing unit 32 of the holder 30 extend, the curvature of the first grating 21, etc. can be maintained before and after the receiving unit 31 and the pressing unit 32 extend (or the curvature of the first grating etc. can be maintained so that the problem of vigletting does not occur) and it is possible to prevent the problem of vigletting from occurring due to rise in temperature.

According to the above described embodiment, the example of the ray source grating 20, the first grating 21, and the second grating 22 formed with the silicon wafer is described. Alternatively, the present invention can be applied when the above gratings are formed from different material.

The detailed configuration and operation can be suitably modified without leaving the scope of the present invention.

What is claimed is:

1. An X-ray Talbot capturing apparatus comprising:
   a plurality of gratings in which slits are formed;
   a radiation source which irradiates radiation to pass through the plurality of gratings;
   a radiation detector which captures a moire image; and
   a holder which holds the gratings,
   wherein, the holder includes a receiving unit including a receiving surface with a curve and a pressing unit including a pressing surface with a curve;
   each grating is held between the receiving surface of the receiving unit and the pressing surface of the pressing unit of the holder and bent in an arc shape with a point of the radiation source as a center;
   an elastic member is positioned between a first surface of the grating and the pressing surface of the pressing unit or a second surface of the grating opposite of the first surface and the receiving surface of the receiving unit; and
   an opening is provided in each of the receiving unit and the pressing unit of the holder and the elastic member so as not to block radiation irradiated on the grating.

2. The X-ray Talbot capturing apparatus according to claim 1, wherein, the receiving surface of the receiving unit and the pressing surface of the pressing unit of the holder are bent in an arc shape with the point of the radiation source as the center.

3. The X-ray Talbot capturing apparatus according to claim 1, wherein, at least one of the receiving surface of the receiving unit or the pressing surface of the pressing unit of the holder is bent in an arc shape with the point of the radiation source as the center; and the grating is pressed entirely against the receiving surface or the pressing surface bent in the arc shape by the elastic member.

4. The X-ray Talbot capturing apparatus according to claim 1, wherein, an edge of the elastic member is made so as not to be outside an edge of the receiving surface of the receiving unit of the holder and an edge of the pressing surface of the pressing unit of the holder in contact with the grating.

5. The X-ray Talbot capturing apparatus according to claim 1, wherein, the receiving unit of the holder is connected to the pressing unit with screws in an entire circumference of a periphery with the grating and the elastic member placed in between.

6. The X-ray Talbot capturing apparatus according to claim 1, wherein, the receiving surface of the receiving unit of the holder or the pressing surface of the pressing unit in contact with the grating are processed so as to slide easily.

7. The X-ray Talbot capturing apparatus according to claim 1, wherein, an absolute value of a difference of a thermal expansion coefficient of the receiving unit and the pressing unit of the holder with respect to the thermal expansion coefficient of the grating is equal to or less than $4 \times 10^{-6}$.

8. The X-ray Talbot capturing apparatus according to claim 1, wherein, hardness of the elastic member is a durometer hardness equal to or less than A15.

9. The X-ray Talbot capturing apparatus according to claim 1, wherein, the elastic member has a concave unit or a hole formed in a surface in contact with the receiving unit or the pressing unit of the holder.

10. The X-ray Talbot capturing apparatus according to claim 1, wherein, the receiving unit of the holder is formed with material including a thermal expansion coefficient larger than a thermal expansion coefficient of the pressing unit.

* * * * *